United States Patent [19]
Driscoll et al.

[11] Patent Number: 4,814,491
[45] Date of Patent: Mar. 21, 1989

[54] HEMIACETALS OF GLYOXYLIC ESTERS AND A PROCESS FOR THE ISOLATION OF GLYOXYLIC ESTERS

[75] Inventors: Robert K. Driscoll, Frankfurt am Main; Ernst I. Leupold, Neu-Anspach; Joachim Schütz, Hofheim am Taunus, all of Fed. Rep. of Germany

[73] Assignee: Hoeschst Aktiengesellschaft, Frankfurt am Main, Fed. Rep. of Germany

[21] Appl. No.: 193,225

[22] Filed: May 11, 1988

Related U.S. Application Data

[63] Continuation of Ser. No. 6,975, Jan. 22, 1987.

[30] Foreign Application Priority Data

Jan. 25, 1986 [DE] Fed. Rep. of Germany ....... 3602274

[51] Int. Cl.$^4$ .............................................. C07C 69/66
[52] U.S. Cl. .................................................... 560/186
[58] Field of Search ......................................... 560/186

[56] References Cited

U.S. PATENT DOCUMENTS

| | | | |
|---|---|---|---|
| 4,156,093 | 5/1979 | Christidis | 560/186 |
| 4,443,623 | 4/1984 | Photis | 560/170 |
| 4,692,547 | 9/1987 | Driscoll et al. | 560/186 |

FOREIGN PATENT DOCUMENTS

| | | | |
|---|---|---|---|
| 517825 | 10/1955 | Canada | 560/186 |
| 0140866 | 5/1985 | European Pat. Off. | |
| 0149456 | 7/1985 | European Pat. Off. | |
| 1004158 | 3/1957 | Fed. Rep. of Germany | 560/186 |
| 2811480 | 9/1978 | Fed. Rep. of Germany | 560/186 |
| 61-50941 | 3/1986 | Japan | 560/186 |

OTHER PUBLICATIONS

Oroshnik, W. et al., J. Amer. Chem. Soc. 63, 3338–3339 (1941).

*Primary Examiner*—Bruce D. Gray

[57] ABSTRACT

The invention relates to hemiacetals of glyoxylic esters and to a process for obtaining a glyoxylic ester having a $C_1$ to $C_4$ ester group from a mixture which essentially contains a glyoxylic ester of this type plus water and/or a $C_1$ to $C_4$ alcohol ROH. In this, the glyoxylic ester and the water and/or the alcohol are partly or completely in a chemically bonded form. A higher alcohol R'OH having a boiling point above 180° C. is added, and distillation is carried out under a pressure not exceeding 800 mbar to remove first the water and/or the alcohol ROH and then the glyoxylic ester.

7 Claims, No Drawings

HEMIACETALS OF GLYOXYLIC ESTERS AND A PROCESS FOR THE ISOLATION OF GLYOXYLIC ESTERS

The present invention relates to a process for the isolation of a glyoxylic ester having a $C_1$ to $C_4$ ester group from a mixture which essentially contains a glyoxylic ester of this type plus water and/or a lower alcohol having 1 to 4 carbon atoms. Thus, essentially present in addition to the glyoxylic ester are water or a lower alcohol, or both, and they are partly or completely in chemically bonded form, namely as hemiacetal, hydrate or oligomer of the glyoxylic ester.

Mixtures of this type result from, for example, the reaction of a lower alcohol ROH with aqueous glyoxylic acid when the water is simultaneously distilled out, the main product being the hemiacetal ROCH(OH)COOR of the glyoxylic ester, and a byproduct being the corresponding full acetal. In this case the ester group of the hemiacetal is derived from the same alcohol ROH as is the hemiacetal group. The situation is similar on condensation of the reaction mixture resulting from the oxydehydrogenation of glycolic esters in the gas phase at high conversion (European Pat. No. A2-0,149,456). In this case, the reaction mixture additionally contains small proportions of unreacted glycolic ester.

Moreover, mixtures containing glyoxylic esters and water and/or a lower alcohol (in free or bonded form) are produced when the glyoxylic ester of a particular alcohol is reacted with another lower alcohol. Hence in this case the ester group of the hemiacetal is derived from an alcohol different from that of the hemiacetal group.

To date, in the literature it is regarded as difficult to obtain pure glyoxylic esters completely from their hemiacetals, inter alia because of the high reactivity of the compounds. In general, this cleavage and separation is achieved by the action of stoichiometric amounts of $P_2O_5$ followed by distillation. This procedure is described in, for example, Oroshnik et al., J. Amer. Chem. Soc. 1941, 63, 3338. Although this method is effective, it does not qualify for a large-scale process because of the high costs and because of the waste problems associated therewith.

There is a description, in European Pat. No. A1-0,140,866, of a process for obtaining pure glyoxylic esters from mixtures which contain glyoxylic ester, water and lower alcohol plus various impurities but, in addition, at least 1 mole of glycolic ester per mole of glyoxylic ester. Mixtures of this type result from the oxydehydrogenation of glycolic esters to give glyoxylic esters in the gas phase, followed by condensation, if the oxydehydrogenation conversion is low. Where necessary, the molar ratio of glycolic ester to glyoxylic ester is adjusted to at least 1:1 by addition of glycolic ester. However, using this method it is possible to obtain only about 70% of the glyoxylic ester which is present in free or bonded form in the initial mixture (Example 1).

It has now been found that glyoxylic esters can be obtained, essentially completely, from a mixture with water and/or a lower alcohol, the mixture containing little or no glycolic ester.

The invention relates, on the one hand, to a process for obtaining a glyoxylic ester having a $C_1$ to $C_4$ ester group from a mixture which essentially contains a glyoxylic ester of this type plus water and/or a $C_1$ to $C_4$ alcohol ROH, the glyoxylic ester and the water and/or the alcohol being present partly or completely in chemically bonded form, which comprises addition of a higher alcohol R'OH having a boiling point above 180° C., and distillation out, under a pressure not exceeding 800 mbar, of first the water and/or the alcohol ROH and then the glyoxylic ester.

The first step after addition of the higher alcohol R'OH, or during its addition, that is to say the distillation out of water and/or alcohol ROH, and the second step, that is to say the distillation out of the glyoxylic ester, are preferably carried out continuously in two columns or thin-film evaporators connected in series. It is, however, also possible to operate discontinuously, in which case one column or one thin-film evaporator generally suffices, the two steps then being carried out successively therein. The continuous procedure is preferred because the shorter hold-up times cause fewer undesired side reactions. It is preferable to use an alcohol R'OH having a boiling point above 200° C., because then the glyoxylic ester is obtained essentially completely.

The terms glyoxylic ester, alcohol and water relating to the mixture used in the process according to the invention are intended, as already indicated above, to embrace also the chemically bonded forms of these substances, such as glyoxylic ester hydrate, glyoxylic ester oligomers and glyoxylic ester hemiacetal. If, in addition, there are small amounts of glycolic ester present, these may also be in the form of glycolic ester hemiacetal of the glyoxylic ester (because glycolic ester also has a free hydroxyl group). The content of glycolic ester should not exceed 0.5 mole per mole of glyoxylic ester. Particularly suitable starting mixtures are those which contain no more than 0.2 mole, in particular no more than 0.1 mole, of glycolic ester per mole of glyoxylic ester.

The alkyl radicals of the glyoxylic ester, of the alcohol ROH and, where appropriate, of the glycolic ester have 1 to 4 carbon atoms and can be identical or different. They are preferably identical, in particular they are all methyl. The term "lower alcohol having 1 to 4 carbon atoms" is not intended to embrace the methyl and ethyl esters of glycolic acid (which also contain a free hydroxyl group and have 3 and 4 carbon atoms respectively), but only methanol, ethanol, the propanols and the butanols.

The first step in the process according to the invention relates to the removal of water and/or lower alcohol ROH by distillation under a pressure not exceeding 800 mbar, preferably about 15–530 mbar. This entails the higher alcohol R'OH being added beforehand or simultaneously. It can, for example, be introduced into the reaction mixture resulting from the abovementioned oxydehydrogenation of glycolic ester in the gas phase, and the introduction can be effected before or after condensation of this reaction mixture.

In general, the molar ratio of R'OH to glyoxylic ester ought to be at least 1.0:1 when monohydric alcohols are used. If, however, alcohols having several OH groups, such as diethylene glycol or triethylene glycol, are used as R'OH, satisfactory results can be achieved even with molar ratios distinctly below 1.0:1, namely from about 0.5:1. The removal of water and alcohol (ROH) becomes more nearly complete as the molar ratio increases.

Thus, with monohydric alcohols R'OH the molar ratio is generally in the range from about 1.0:1 to about 4.0:1. The preferred molar ratio is in the range from 1.0:1 to 2.5:1.

With polyhydric alcohols, the molar ratio is generally selected to be from 0.5:1 to 4.0:1, preferably 0.5:1 to 2.0:1.

Molar ratios above 4.0:1 are, of course, also suitable, but they entail no distinct improvement in the removal of water and alcohol, and they give rise to higher distillation costs.

Of course, the alcohols R'OH which are to be used must not be solid under the envisaged operating conditions. Those with melting points below 50° C. are preferred. The following alcohols are particularly suitable, as long as they have a boiling point above 180° C., preferably above 200° C.:

(a) Straight-chain or branched alkanols having a maximum of 16 carbon atoms.
(b) Polyglycols HO$-(CH_2CH_2O)_n$H with n=2 to 24.
(c) Polyglycol monoethers HO$-(CH_2CH_2O)_n$R" with n=2 to 24, R" being a straight-chain or branched alkyl radical having a maximum of 4 carbon atoms.

It is also possible to use mixtures of the said alcohols. Particularly suitable are 1-decanol, 2-decanol, diethylene glycol, triethylene glycol, diethylene glycol monobutyl ether and triethylene glycol monomethyl ether.

The bottom product from the first step essentially contains glyoxylic ester and R'OH, the glyoxylic ester largely being in the form of the hemiacetal with R'OH.

The second step of the process comprises the obtaining of pure glyoxylic ester by distillation from this bottom product. Pure glyoxylic ester is obtained overhead, while the alcohol R'OH is left behind. The latter can be returned to the first step.

The pressure in the second step once again does not exceed 800 mbar, preferably being about 15 to 530 mbar. In principle, it is possible to distil the glyoxylic ester completely off from the alcohol R'OH. However, this requires relatively high temperatures, which signifies an increased risk of decomposition. For this reason, the distillation out of the glyoxylic ester is preferably not taken entirely to completion. The bottom product which remains behind then contains not only the alcohol R'OH but also small amounts of glyoxylic ester. This bottom product can be used anew in the process according to the invention.

The invention also relates to hemiacetals of glyoxylic esters, of the general formula R'"OCH(OH)COOR*, R* being a straight-chain or branched alkyl radical having 1 to 4 carbon atoms, preferably the methyl radical, and R'" having one of the following structures:

(a) A straight-chain or branched alkyl radical having 9 to 16 carbon atoms, preferably 1-decyl, 2-decyl or 1-dodecyl.
(b) $-(CH_2CH_2O)_n$H with n=2 to 24, preferably n=2 or 3.
(c) $-(CH_2CH_2O)_n$R" with n=2 to 24, preferably n=2 or 3, R" being a straight-chain or branched alkyl radical having a maximum of four carbon atoms.

It is possible to prepare the free glyoxylic esters from these hemiacetals by heating and distilling the hemiacetals.

The free glyoxylic esters are, by reason of their high reactivity, valuable starting materials and intermediates for a number of syntheses of pharmaceutically active compounds such as, for example, allantoin, substituted glycines or alkaloids (such as, for example, tetrahydroisoquinoline alkaloids).

Recently, it has been suggested that glyoxylic esters be used for preparing polymeric, biodegradable substitutes for phosphates for detergents.

The examples which follow are intended to illustrate the invention in detail.

EXAMPLE 1

1 mol (88 g) of methyl glyoxylate was distilled under 130 mbar through a Claisen distillation apparatus into a receiver containing a stirrer and 1 mol of the relevant alcohol R'OH. This mixture was placed in the bottom of a distillation column (length 450 mm, diameter 20 mm, packing: Braunschweiger glass helices, reflux ratio 4:1) and distilled under constant pressure. During the distillation, samples were frequently taken from the column head and analyzed by gas chromatography or by classical methods. The first fractions contained almost exclusively methyl glyoxylate. The distillation was continued until fractions at the head were found to contain small amounts of the relevant R'OH. The results of experiments with various operating pressures and with various alcohols R'OH are shown in Table 1. Distillations under 80 mbar resulted in high purities (around 97.5%); the impurities were essentially water, methanol and R'OH. It is evident from the results that the amount of methyl glyoxylate isolated distinctly increases as the boiling point of R'OH increases. Only considerably lower yields than with the process according to the invention can be obtained from the comparison experiment 1a with methyl glycolate as R'OH (as specified in European Pat. No. A1-0,140,866). Particularly good results were attained with the preferred alcohols in experiments (1e) to (1j).

TABLE 1

| | Alcohol R'OH | Boiling point under atmospheric pressure | Distillation pressure (mbar) | OHCCOOCH$_3$ yield (%) | OHCCOOCH$_3$ content of the distillate (% by wt.) |
|---|---|---|---|---|---|
| a | Methyl glycolate (comparison) | 151° C. | 80 | 32.2 | 97.2 |
| b | 2-Ethylhexanol | 184° C. | 333 | 56.1 | 95.1 |
| | | | 80 | 25.7 | 96.7 |
| c | Diethylene glycol monomethyl ether | 193° C. | 27 | 71.3 | 97.3 |
| d | n-Octanol | 194° C. | 80 | 63.1 | 97.7 |
| e | Diethylene glycol monobutyl ether | 228° C. | 80 | 96.2 | 96.9 |
| f | n-Decanol | 230° C. | 80 | 97.4 | 98.3 |
| g | Diethylene glycol | 245° C. | 80 | 98.1 | 98.4 |
| h | Triethylene glycol monomethyl ether | 249° C. | 80 | 96.2 | 97.1 |
| i | Triethylene glycol | 276° C. | 27 | 97.0 | 98.1 |

TABLE 1-continued

| Alcohol R'OH | Boiling point under atmospheric pressure | Distillation pressure (mbar) | OHCCOOCH$_3$ yield (%) | OHCCOOCH$_3$ content of the distillate (% by wt.) |
| --- | --- | --- | --- | --- |
| j Triethylene glycol mono-n-butyl ether | 282° C. | 80 | 96.0 | 97.6 |

EXAMPLE 2

Methyl glycolate was oxidized by the process described in German Offenlegungsschrift No. 3,417,649, and the discharge from the reactor was condensed. 117 g of diethylene glycol were added for each 100 g of condensate, this resulting in a mixture of the following composition (in % by weight): 36.1% methyl glyoxylate, 7.8% water, 1.3% methanol, 53.9% diethylene glycol and 0.9% others. 80 g per hour of this mixture were preheated to about 70° C. and introduced into the central section of a continuously operated distillation column (length 100 cm, diameter 2 cm, packing: Braunschweiger glass helices). The glass helices were packed to a height of 60 cm in the stripping section and 30 cm in the concentrating section. The column was operated at 40 mbar, and the reflux ratio was 2:1. During the experiment the bottom temperature was about 115° C. Once equilibrium had been reached, 72.6 g of product were obtained per hour in the bottom, the composition being as follows (in % by weight): 39.7% methyl glyoxylate, 0.34% water, 0.14% methanol, 59.4% diethylene glycol and 0.42% others. Thus water and methanol were substantially removed. The column was cleaned and used for the second step.

The bottom product from the first step was used as charge stock for the second step. 66.0 g per hour of this mixture were preheated to about 70° C. and introduced at the same point as in the first step in the central section of the distillation column. The column was operated at 80 mbar, and the reflux ratio was 2:1. The bottom and head temperatures during the experiment were about 167° C. and 51° C. respectively. Once equilibrium had been reached, 25.5 g per hour of head product of the following composition (in % by weight) were obtained: 98.8% methyl glyoxylate, 0.67% water, 0.1% methanol and 0.43% others. In addition, 40.4 g per hour of bottom product of the following composition (in % by weight) were produced: 2.23% methyl glyoxylate, 0.03% water, 0.17% methanol, 97.0% diglycol and 0.57% others.

EXAMPLE 3

The distillation column described in Example 1 was used again for this. The charge stock mixture had the following composition (in % by weight): 29.5% methyl glyoxylate, 1.5% methyl glycolate and 69.0% triethylene glycol mono-n-butyl ether. 250 g of this mixture were introduced into the boiler, and distillation was carried out with a reflux ratio of 4:1 and under a pressure of 80 mbar. The head temperature was about 51° C. while the main fraction was being removed, this being composed of 68.8 g of 97.7% pure methyl glyoxylate. The remaining methyl glyoxylate was isolated as a mixed fraction together with methyl glycolate and triglycol butyl ether.

EXAMPLE 4

200.0 g of a mixture of the following composition (in % by weight) were introduced into the boiler of a distillation column (length 100 cm, diameter 2 cm, packing: Braunschweiger glass helices): 95.2% CH$_3$OCH(OH)—COOCH$_3$, 2.1% (CH$_3$O)$_2$CH—COOCH$_3$, 1.7% OCH—COOH, 0.5% CH$_3$OH and 0.5% water. The mixture was distilled under 60 mbar and with a reflux ratio of 3:1 and, at the same time, 180 g of diethylene glycol (120 g/h) were introduced into the top third of the column. After an experiment lasting 1½ hours, the bottom product comprised 327.4 g of a mixture of the following composition (in % by weight): 42.6% CHO—COOCH$_3$, 1.3% (CH$_3$O)$_2$CH—COOCH$_3$, 1.0% OCH—COOH, 0.06% water and 55.0% diglycol, the methyl glyoxylate being predominantly in the form of the hemiacetal with diglycol. 52.6 g of a mixture of the following composition was obtained overhead: 98.5% by weight methanol and 1.5% by weight water. The bottom product essentially contained methyl glyoxylate and diglycol.

EXAMPLE 5

0.74 mol (65 g) of methyl glyoxylate was distilled under 100 mbar in a Claisen distillation apparatus into a receiver containing a stirrer and 0.74 mol (78.4 g) of diethylene glycol. The resulting hemiacetal was characterized by its $^{13}$C NMR spectrum (recorded in acetone-d$_6$).

$$\begin{array}{c} \phantom{xxx} \text{OH} \\ \text{a} \quad \text{b} \quad \text{c} \diagup \\ \text{CH}_3\text{OOC—CH} \\ \phantom{xxxxxx} \diagdown \\ \phantom{xxxxxx} \text{OCH}_2\text{CH}_2\text{OCH}_2\text{CH}_2\text{OH} \\ \phantom{xxxxxx} \text{d} \quad \text{e} \quad \text{f} \quad \text{g} \end{array}$$

| Carbon atom | Chemical shift (ppm) | Relative intensity |
| --- | --- | --- |
| a | 52.4 | 1 |
| b | 169.7 | 1 |
| c | 93.3 | 1 |
| d | 67.2 | 1 |
| e | 70.5 | 1 |
| f | 72.7 | 1 |
| g | 61.5 | 1 |

No other peaks are present in the spectrum. The number of peaks, the peak positions and the relative intensities are consistent with the hemiacetal structure. Diglycol would exhibit two peaks, namely at 61.4 and 72.6 ppm, whereas the hemiacetal exhibits four O—CH$_2$ signals at 61.5, 72.7, 67.2 and 70.5 ppm) (d to g). The signal at 93.3 ppm is characteristic for a hemiacetal carbon atom of the following structure:

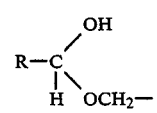

R being COOCH$_3$

No peaks characteristic of unreacted methyl glyoxylate were present.

EXAMPLE 6

0.34 mol (29.9 g) of methyl glyoxylate were distilled under 130 mbar in a Claisen distillation apparatus in a receiver containing a stirrer and 0.34 mol (55.1 g) of diethylene glycol mono-n-butyl ether. The resulting hemiacetal was characterized by its $^{13}$C NMR spectrum (recorded in acetone-$d_6$):

$$\begin{array}{c} \text{a} \quad \text{b c} \diagup \text{OH} \\ CH_3OOCC \\ \quad \mid \diagdown \quad \text{h [d,e,f and g]} \quad \text{i} \quad \text{j} \quad \text{k} \\ \text{H} \quad OCH_2CH_2OCH_2CH_2OCH_2CH_2CH_2CH_3 \end{array}$$

| carbon atom | chemical shift (ppm) | signals | relative intensity |
|---|---|---|---|
| a | 52.2 | 1 | 1 |
| b | 169.4 | 1 | 1 |
| c | 93.4 | 1 | 1 |
| d + e + f + g | 70.3 to 71.0 | 4 | Σ = 4 |
| h | 67.3 | 1 | 1 |
| i | 32.1 | 1 | 1 |
| j | 19.6 | 1 | 1 |
| k | 14.0 | 1 | 1 |

No other peaks are present in the spectrum. The number of peaks, the peak positions and the relative intensities are consistent with the hemiacetal structure. The signal at 93.4 ppm is characteristic of a hemiacetal carbon atom of the following structure:

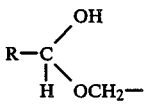

R being COOCH$_3$

EXAMPLE 7

0.35 mol (30.8 g) of methyl glyoxylate were distilled under 100 mbar in a Claisen distillation apparatus into a receiver containing a stirrer and 0.35 mol (55.3 g) of n-decanol. The resulting hemiacetal was characterized by its $^{13}$C NMR spectrum (recorded in acetone-$d_6$):

$$\begin{array}{c} \text{a} \quad \text{b} \quad \text{c} \diagup \text{OH} \\ CH_3OOC{-}C \\ \quad \mid \diagdown \quad \text{d} \quad \text{e} \quad \text{f} \quad (\quad \text{e} \quad ) \quad \text{g} \quad \text{h} \quad \text{i} \\ \text{H} \quad OCH_2CH_2CH_2CH_2CH_2CH_2CH_2CH_2CH_3 \end{array}$$

| carbon atom | chemical shift (ppm) | signals | relative intensity |
|---|---|---|---|
| a | 52.1 | 1 | 1 |
| b | 170.1 | 1 | 1 |
| c | 93.3 | 1 | 1 |
| d | 68.1 | 1 | 1 |
| e | 29.8–30.2 | 5 | Σ = 5 |
| f | 26.6 | 1 | 1 |
| g | 32.4 | 1 | 1 |
| h | 23.1 | 1 | 1 |
| i | 14.2 | 1 | 1 |

No other peaks are present in the spectrum. The number of peaks, the peak positions and the relative intensities are consistent with the hemiacetal structure.

We claim:

1. A process for obtaining uncombined glyoxylic ester having a $C_1$ to $C_4$ ester group from a mixture which contains a glyoxylic ester having a $C_1$ to $C_4$ ester group and water and/or a $C_1$ to $C_4$ alcohol ROH, the glyoxylic ester and the water and/or the alcohol ROH being present in said mixture partly or completely in combined form, as glyoxylic ester hydrate, glyoxylic ester hemiacetal or glyoxylic ester oligomers, which process comprises introducing into the mixture a higher alcohol R'OH having a boiling point above 180° C. and a melting point below 50° C., and distilling out, under a pressure not exceeding 800 mbar, first the water and/or the alcohol ROH and then the uncombined glyoxylic ester essentially free of glyoxylic ester hydrate, glyoxylic ester hemiacetal, and glyoxylic acid ester oligomers; the higher alcohol R'OH being a higher alkanol, a polyglycol or a polyglycol ether.

2. The process as claimed in claim 1, wherein said higher alcohol has a boiling point above 200° C.

3. The process as claimed in claim 1, wherein said higher alcohol R'OH is:
   (a) a straight-chain or branched higher alkanol having a maximum of 16 carbon atoms,
   (b) a polyglycol of the formula HO$-$(CH$_2$CH$_2$)O$_{\overline{n}}$H, n being a number from 2 to 24,
   (c) a polyglycol monoether of the formula HO$-$(CH$_2$CH$_2$O)$_{\overline{n}}$R", wherein n is a number from 2 to 24 and R" is a straight-chain or branched alkyl radical having a maximum of 4 carbon atoms, or a mixture of said higher alcohols.

4. The process as claimed in claim 1, wherein the process is operated under a pressure of about 15 to about 530 mbar.

5. The process as claimed in claim 1, wherein said glyoxylic ester is methyl glyoxylate, and said ROH is methanol.

6. A process for isolating uncombined glyoxylic ester having a $C_1$ to $C_4$ ester group from a mixture consisting essentially of a glyoxylic ester having a $C_1$ to $C_4$ ester group and water and/or a $C_1$ to $C_4$ alcohol, ROH, the glyoxylic ester and the water and/or ROH being present in said mixture at least partly in combined form, as glyoxylic ester hydrate, glyoxylic ester hemiacetal or a glyoxylic ester oligomer, which process comprises:
   introducing a higher alcohol consisting essentially of a higher alkanol, a polyglycol, a polyglycol monoether, or a mixture thereof, said higher alkanol, polyglycol or polyglycol ether having a melting point below 50° C. and a boiling point above 180° C.;
   distilling out, under a pressure not exceeding 800 mbar, the ROH and/or water, thereby forming a bottom product which consists essentially of glyoxylic ester and said higher alcohol, at least a portion of the glyoxylic ester being in the form of a hemiacetal of said higher alcohol;
   distilling said bottom product under a pressure not exceeding 800 mbar, whereby the glyoxylic ester, in uncombined form, essentially free of glyoxylic ester hydrate, glyoxylic ester hemiacetal and glyoxylic ester oligomer, is distilled off from said product and is recovered in said form, and essentially the higher alcohol is left behind.

7. A process as claimed in claim 6 wherein the higher alcohol which is left behind contains a minor amount of undistilled glyoxylic ester, and said higher alcohol which is left behind is returned to the first distilling step for re-use in the process.

* * * * *